US006187042B1

(12) United States Patent
Sheets, Jr. et al.

(10) Patent No.: US 6,187,042 B1
(45) Date of Patent: Feb. 13, 2001

(54) INTRAOCULAR LENS COATING COMPOSITIONS

(75) Inventors: John W. Sheets, Jr.; Albert R. Leboeuf, both of Fort Worth; Anilbhai S. Patel, Arlington; Mutlu Karakelle; Stephen J. Van Noy, both of Fort Worth, all of TX (US)

(73) Assignee: Alcon Laboratories, Inc., Fort Worth, TX (US)

( * ) Notice: Under 35 U.S.C. 154(b), the term of this patent shall be extended for 0 days.

(21) Appl. No.: 09/283,701

(22) Filed: Apr. 1, 1999

Related U.S. Application Data

(60) Provisional application No. 60/081,842, filed on Apr. 15, 1998.

(51) Int. Cl.$^7$ ....................................................... A61F 2/16
(52) U.S. Cl. .......................... 623/6.62; 623/6.6; 623/926
(58) Field of Search ................................... 623/6.62, 6.6, 623/6.57, 6.56, 926; 427/2.24; 526/259

(56) References Cited

U.S. PATENT DOCUMENTS

| | | | |
|---|---|---|---|
| 4,515,794 | 5/1985 | Emery et al. | 514/249 |
| 4,725,276 | 2/1988 | Bissonette et al. | 623/6 |
| 4,846,833 | 7/1989 | Cumming | 623/6 |
| 4,918,165 | 4/1990 | Soll et al. | 530/391 |
| 4,950,290 | 8/1990 | Kamerling | 623/6 |
| 5,002,571 | 3/1991 | O'Donnell, Jr. et al. | 623/6 |
| 5,057,578 | 10/1991 | Spinelli | 525/278 |
| 5,078,740 | 1/1992 | Walman | 623/36 |
| 5,290,892 | 3/1994 | Namdaran et al. | 526/259 |
| 5,331,073 | 7/1994 | Weinschenk, III et al. | 526/264 |
| 5,359,021 | 10/1994 | Weinschenk, III et al. | 526/264 |
| 5,366,501 | 11/1994 | Langerman | 623/6 |
| 5,370,687 | 12/1994 | Poler | 623/6 |
| 5,371,147 | 12/1994 | Spinelli et al. | 525/288 |
| 5,375,611 | 12/1994 | Lindqvist et al. | 128/898 |
| 5,405,385 | 4/1995 | Heimke et al. | 623/6 |
| 5,470,932 | 11/1995 | Jinkerson | 526/312 |
| 5,494,946 | 2/1996 | Christ et al. | 523/113 |
| 5,549,670 | 8/1996 | Young et al. | 623/6 |
| 5,576,345 | 11/1996 | Mansson et al. | 514/449 |
| 5,593,438 | 1/1997 | Akhavi et al. | 623/6 |
| 5,618,316 | 4/1997 | Hoffman et al. | 623/6 |
| 5,693,094 | 12/1997 | Young et al. | 623/6 |
| 5,693,095 | 12/1997 | Freeman et al. | 623/6 |
| 5,733,276 | 3/1998 | Belkin | 606/6 |
| 5,869,549 | 2/1999 | Christ et al. | 523/212 |
| 5,876,438 | 3/1999 | Kelleher et al. | 623/4 |
| 5,891,931 | * 4/1999 | Leboeuf et al. | 522/64 |
| 6,027,531 | 2/2000 | Tassignon | 623/6 |

FOREIGN PATENT DOCUMENTS

| | | |
|---|---|---|
| 0 559 820 B1 | 9/1993 | (EP) . |
| 0 611 379 B1 | 5/1996 | (EP) . |
| 0 781 777 A1 | 7/1997 | (EP) . |
| 0 675 910 B1 | 9/1997 | (EP) . |
| 0 904 747 A2 | 3/1999 | (EP) . |
| 0 916 320 A2 | 5/1999 | (EP) . |
| WO 94/11764 | 5/1994 | (WO) . |
| WO 96/25962 | 8/1996 | (WO) . |
| WO 96/34629 | 11/1996 | (WO) . |
| WO 97/20851 | 6/1997 | (WO) . |
| WO 98/15238 | 4/1998 | (WO) . |
| 99/62435 | 12/1999 | (WO) . |

OTHER PUBLICATIONS

Cunanan et al., "An In Vitro Test Method to Study Posterior Capsular Opacification," *Investigative Ophthalmology & Visual Science*, vol. 38(4), p. S178 (1997).

Gabriel et al., "In Vitro Adherence of *Pseudomonas aeruginosa* to Four Intraocular Lenses," *J. Cataract Refractive Surg*, vol. 24, pp. 124–129 (1998).

Hollick et al., "Lens Epithelial Cells Regression on the Posterior Capsule: A 2 Year Prospective, Randomised Trial With Three Different IOL Materials," *Investigative Ophthalmology & Visual Science*, vol. 38(4), p. S19 (1997).

Linnola et al., "Acrylate Intraocular Lenses (IOLs) Hinder Posterior Migration of Epithelium; Activity Tested by Corneal Tissue Cultures," *ESCRS Abstracts*, p. 120 (1997).

Linnola, "Sandwich Theory: Bioactivity–based Explanation for Posterior Capsule Opacification," *J. Cataract Refract. Surg.*, vol. 23, pp. 1539–1542 (1997).

Mandle, "Acrylic Lenses Cause Less Posterior Capsule Opacification than PMMA, Silicone IOLs," *Ocular Surgery News*, vol. 14(15), p. 23 (1996).

Nagamoto et al., "Effect of Intraocular Lens Design on Migration of Lens Epithelial Cells Onto the Posterior Capsule," *J. Cataract Refract Surg.*, vol. 23, pp. 866–872 (1997).

(List continued on next page.)

*Primary Examiner*—Paul B. Prebilic
(74) *Attorney, Agent, or Firm*—Patrick M. Ryan

(57) ABSTRACT

Intraocular lens coating compositions for reducing the risk of posterior capsule opacification are disclosed. The coating materials, which differ from the substrate material, consist essentially of at least two aryl acrylic hydrophobic monomers of the formula (I)

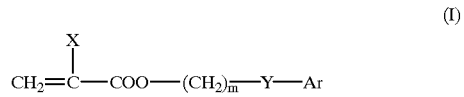

wherein:
  X is H or $CH_3$;
  m is 0–10;
  Y is nothing, O, S, or NR wherein R is H, $CH_3$, $C_nH_{2n+1}$ (n=1–10) iso $OC_3H_7$, $C_6H_5$, or $CH_2C_6H_5$;
  Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$.

7 Claims, No Drawings

OTHER PUBLICATIONS

Nagata et al., "Adhesiveness of AcrySof to a Collagen Film," *J. Cataract Refract. Surg.*, vol. 24, pp. 367–370 (1998).

Nagata et al., "Optic Sharp Edge or Convexity: Comparison of Effects of Posterior Capsular Opacification," *Jpn J. Ophthal.*, vol. 40, pp. 397–403 (1996).

Nishi et al., Inhibition of Migrating Lens Epithelial Cells By Blocking The Adhesion Molecule Integrin: A Preliminary Report, *J. Cataract Refract. Surg*, vol. 23 (1997).

Oshika et al., "Adhesion of Lens Capsule to Intraocular Lenses of Polymethylmethacrylate, Silicone and Acrylic Foldable Materials: An Experimental Study," *British Journal of Ophthalmology*, vol. 82, pp. 549–553 (1998).

Oshika et al., "Incision/Phacoemulsification," Symposium on Cataract, IOL and Refractive Surgery, Jun., 1996.

Oshika et al., "Two Year Clinical Study of a Soft Acrylic Intraocular Lens," *J. Cataract Refract. Surg.*, vol. 22, pp. 104–109 (1996).

Pande et al., "High-Resolution Digital Retroillumination Imaging of the Posterior Lens Capsule After Cataract Surgery," *J. Cataract Refract. Surg.*, vol. 23, pp. 1521–1527 (1997).

Pande et al., "Posterior Capsular Opacification With PMMA, Silicone and Acrysof Intraocular Lenses: A Prospective Randomized Clinical Trial," *Investigative Ophthalmology & Visual Science*, vol. 36(4), p. S397 (1995).

Reich et al., "Intraocular-Lens-Endothelial Interface: Adhesive Force Measurements," *J. of Biomedical Materials Research*, vol. 18, pp. 737–744 (1984).

Saika et al., "Cell Proliferation on the Outer Anterior Capsule Surface After Extracapsular Lens Extraction in Rabbits," *J. Cataract Refractive Surg.* vol. 23, pp. 1528–1531 (1997).

Ursell et al., Anterior Capsule Stability in Eyes With Intraocular Lenses Made of Poly(methyl methacrylate), Silicone, and AcrySof, *J. Cataract Refractive Surg.*, vol. 23, pp. 1532–1538 (1997).

Ursell et al., "Relationship Between Intraocular Lens Biomaterials and Posterior Capsule Opacification," *J. Cataract Refractive Surg.* vol. 24, pp. 352–360 (1998).

Ursell et al., "The In Vivo Movement of Cells on the Surface of Intraocular Lenses in Humans Observed with Sequential Specular Photomicrography," *Investigative Ophthalmology & Visual Science*, vol. 36(4), S795 (1995).

Werner et al., "Endothelial Damage Caused by Uncoated and Fluorocarbon-Coated Poly(methyl methacrylate) Intraocular Lenses," *J. Cataract Refractive Surgery*, vol. 23, pp. 1013–1019 (1997).

Yang et al., "Membrane Formation and Cellular Response on the Surface of Lenses Implanted in Rabbit Eyes," *J. Cataract Refractive Surg.*, vol. 23, pp. 1265–1270 (1997).

Johnston et al., "In Vitro Protein Adsorption to 2 Intraocular Lens Materials," *J. Cataract & Refractive Surgery*, vol. 25, pp. 1109–1115 (1999).

Kanagawa et al., "Presence and distributio of fibronectin on the surface of implanted intraocular lenses in rabbits," *Graefe's Archive for Clinical & Exp. Ophthalmology*, vol. 228, pp. 398–400 (1990).

Linnola et al., "Intraocular lens bioactivity tested using rabbit corneal tissue cultures," *J. Cataract & Refractive Surgery*, vol. 25, pp. 1480–1485 (1999).

Liu et al., "A Study of Human Lens Cell Growth In Vitro," *Investigative Oph. & Visual Science*, vol. 37(5), pp. 906–914 (1996).

Linnola et al., "Adhesion of soluble fibronectin, laminin, and collagen type IV to intraocular lens materials," *J. of Cataract & Refractive Surgery*, vol. 25 (11), pp. 1486–1491 (1999).

* cited by examiner

INTRAOCULAR LENS COATING COMPOSITIONS

This application claims priority from U.S. Provisional Patent Application Ser. No. 60/081,842, filed Apr. 15, 1998.

FIELD OF THE INVENTION

This invention relates to intraocular lenses. In particular, the present invention relates to intraocular lens coating compositions for reducing the risk of posterior capsule opacification.

BACKGROUND OF THE INVENTION

Foldable intraocular lens ("IOL") materials can generally be divided into three categories: silicone materials, hydrogel materials, and non-hydrogel acrylic materials. Many materials in each category are known. See, for example, Foldable Intraocular Lenses, Ed. Martin et al., Slack Incorporated, Thorofare, N.J. (1993). Biocompatibility varies among different IOL materials within and among each category.

One measure of biocompatability for an IOL can be the incidence of posterior capsule opacification ("PCO"). A number or factors may be involved in causing and/or controlling PCO. For example, the design and edge sharpness of an IOL may be a factor. See, Nagamoto et al., J. Cataract Refract. Surg., 23:866–872 (1997); and Nagata et al., Jpn. J. Ophthalmol., 40:397–403 (1996). See, also, U.S. Pat. Nos. 5,549,670 and 5,693,094. Another factor appears to be the lens material itself. See, for example, Mandle, "Acrylic lenses cause less posterior capsule opacification than PMMA, silicone IOLs," Ocular Surgery News, Vol. 14. No. 15, p.23 (1996). See, also, Oshika, et al., "Two Year Clinical Study of a Soft Acrylic Intraocular Lens," J. Cataract. Refract. Surg., 22:104–109 (1996); and Ursell et al., "Relationship Between Intraocular Lens Biomaterials and Posterior Capsule Opacification," J. Cataract Refract. Surg., 24:352–360 (1998).

One method of addressing the PCO problem involves administering a pharmaceutical agent to the capsular bag area at the time of, or immediately after, extracapsular cataract extraction. See, for example, U.S. Pat. Nos. 5,576,345 (pharmaceutical agent=the cytotoxic agent taxol or an ophthalmically acceptable derivative); 4,515,794; and 5,370,687. Alternatively, the pharmaceutical agent may be tethered to the surface of the IOL material. See, for example, U.S. Pat. No. 4,918,165. The pharmaceutical agents are intended to kill or prevent the growth of proliferating cells that might cause PCO or "secondary cataracts." Yet another method involves the physical destruction or removal of lens epithelial cells. See, Saika et al., J. Cataract Refract. Surg., 23:1528–1531 (1997).

Another method of addressing PCO is the prophylactic laser therapy method disclosed in U.S. Pat. No. 5,733,276. According to this method, the lens capsule is irradiated with laser irradiation to destroy cells which remain in the lens capsule after extraction of a cataract.

Other methods theorized for reducing the risk of PCO involve adhering the posterior capsule to the IOL at the time of implantation, as in U.S. Pat. No. 5,002,571. According to the '571 patent, a non-biological glue or, preferably, a biological glue, such as fibrin, collagen, or mussel glue, is used to adhere the posterior lens capsule to the posterior surface of an IOL. The glue may be applied over the entire posterior surface of the IOL or just as an annulus around the outer perimeter of the posterior surface of the IOL.

In contrast, U.S. Pat. No. 5,375,611 discloses a method of reducing the risk of PCO by preventing the adherence of the posterior capsule to the IOL. According to the '611 patent, the posterior surface of the lens capsule itself is chemically modified at the time of extracapsular cataract extraction. The chemical modification is achieved by depositing a water-insoluble stable or permanent layer of a cell attachment preventing compound onto the posterior surface of the lens capsule. The stable or permanent layer may be a polymer, such as olyethylene glycol, polysaccharides, polyethylenepropylene gylcol, and polyvinyl lcohols.

What is needed is a method of making lOLs made of materials having relatively high PCO rates more biocompatible by reducing the risk of PCO.

SUMMARY OF THE INVENTION

The present invention relates to IOL coating compositions for making IOL materials more biocompatible. More specifically, the present invention relates to a coated intraocular lens comprising a substrate material and a coating material for making the intraocular lens more biocompatible and reducing the risk of posterior capsule opacification, wherein the coating material is different than the substrate material and the coating material consists essentially of at least two aryl acrylic hydrophobic monomers.

The present invention also relates to a method for reducing the risk of PCO. The method comprises implanting an IOL containing a posterior surface coating consisting essentially of at least two aryl acrylic hydrophobic monomers.

The present invention also relates to a method of applying coating compositions comprising at least two aryl acrylic hydrophobic monomers to an IOL. The method of applying the coating comprises the steps of polymerizing the coating material to form an uncross-linked polymer, dissolving the uncross-linked polymerized material to form a coating solution, applying the coating solution to the IOL, and securing the coating to the IOL's surface.

DETAILED DESCRIPTION OF THE INVENTION

According to the present invention, lOL's are coated with a composition consisting essentially of at least two monomers of Formula I below.

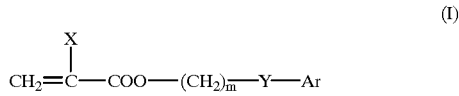

(I)

wherein:

X is H or $CH_3$;

m is 0–10;

Y is nothing, O, S, or NR wherein R is H, $CH_3$, $C_nH_{2n+1}$ (n=1–10) iso $OC_3H_7$, $C_6H_5$, or $CH_2C_6H_5$;

Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$.

Monomers of Formula I are known and include, but are not limited to: 2-phenoxyethyl acrylate; 2-phenylethylthio acrylate; 2-phenylethylamino acrylate; phenyl acrylate; benzyl acrylate; 2-phenylethyl acrylate; 3-phenylpropyl acrylate; 3-phenoxypropyl acrylate; 4-phenylbutyl acrylate; 4-phenoxybutyl acrylate; 4-methylphenyl acrylate; 4-methylbenzyl acrylate; 2-2-methylphenylethyl acrylate; 2-3-methylphenylethyl acrylate; 2-4-methylphenylethyl acrylate; and their corresponding methacrylate compounds.

These acrylic/methacrylic monomers and others are disclosed in U.S. Pat. No. 5,290,892, the entire contents of which are hereby incorporated by reference.

Preferred monomers of Formula I are those where m is 2–4; Y is nothing or O; and Ar is phenyl. Most preferred are 2-phenylethyl acrylate; 2-phenoxyethyl acrylate; 3-phenylpropyl acrylate; 3-phenoxypropyl acrylate; 4-phenylbutyl acrylate; 4-phenoxybutyl acrylate; and their corresponding methacrylate compounds. The IOL coating compositions of the present invention preferably contain at least one monomer of Formula I that is a methacrylate monomer ($X=CH_3$) and at least one monomer of Formula I that is an acrylate monomer ($X=H$). Most preferred are coating compositions consisting essentially of at least one monomer of Formula I that is a methacrylate monomer ($X=CH_3$) and at least one monomer of Formula I that is an acrylate monomer ($X=H$), wherein the total amount of the acrylate monomer(s) of Formula I is greater than the total amount of methacrylate monomer(s) of Formula I. In one preferred embodiment, the IOL coating composition consists essentially of 2-phenylethyl acrylate and 2-phenylethyl methacrylate, and more preferably, about 65% (w/w) of 2-phenylethylacrylate and about 30% (w/w) of 2-phenylethyl methacrylate.

The IOL coating compositions also comprise a first stage polymerization initiator selected from the group consisting of thermal initiators and photoinitiators. The first stage polymerization initiator should be chosen such that it can be activated without causing cross-linking. In the event that the IOL coating composition contains a second stage cross-linking agent prior to stage 1 polymerization, the first stage polymerization initiator is selected from the group consisting of low-temperature thermal initiators and photoinitiators. As used herein, "low-temperature thermal initiator" means a thermal initiator that has an activation temperature lower than the activation temperature of the chosen second stage cross-linking agent. Suitable low temperature thermal initiators include azo free-radical initiators, such as 2,2'-azobis(isobutyronitrile) ["AIBN"] and 2,2'-azobis(2,4-dimethylvalerontrile). Suitable photoinitiators include UV- and blue-light photoinitiators. Many such photoinitiators are known. Preferred blue-light photoinitiators are benzoylphosphine oxide initiators, such as 2,4,6-trimethyl-benzoyldiphenylophosphine oxide; bis-(2,6-dichlorobenzoyl)-4-N-propylphenyl-phosphine oxide; and bis-(2,6-dichlorobenzoyl)-4-N-butylphenyl-phosphine oxide. Most preferred are 2,4,6-trimethyl-benzoyldiphenylophosphine oxide, commercially available as Lucirin® TPO from BASF Corporation (Charlotte, N.C.), and Darocur 4265 from Ciba Geigy. See, for example, commonly-assigned, U.S. Pat. No. 5,891,931 the entire contents of which are hereby incorporated by reference.

The amount of the first stage polymerization initiator in the coating compositions of the present invention will depend upon the curing conditions. In general, however, the amount of first stage polymerization initiator contained in the mixture to be polymerized in stage of the present invention will be about 3% (w/w) or less, preferably about 2% (w/w) or less, and most preferably about 1% (w/w).

In addition to the monomers of Formula I and the first stage polymerization initiator, a second stage cross-linking agent is optionally added to the coating compositions of the present invention prior to stage 1 polymerization. If not present during the stage 1 polymerization, then the second stage cross-linking agent is added at the time the stage 1 polymer is dissolved to form a coating solution. Second stage cross-linking agents are selected from the group consisting of dibenzoyl peroxide, substituted dibenzoyl peroxide compounds, and dicumyl peroxide, many of which are commercially available. For example, dicumyl peroxide is available from Hercules Incorporated (Wilmington, Del.). Suitable substituted dibenzoyl peroxide compounds include 2,4-dichlorodibenzoylperoxide. Dicumyl peroxide and dibenzoyl peroxide are preferred for use with coating compositions consisting essentially of 2-phenylethyl acrylate and 2-phenylethyl methacrylate.

Whether added prior to stage 1 polymerization or at the time the stage 1 polymer is dissolved to form a coating solution, the amount of the second stage cross-linking agent contained in the coating compositions of the present invention will depend upon, among other factors, the degree of cross-linking desired. In general, however, the amount of second stage cross-linking agent in necessary to cross-link the coating composition and secure it to the IOL optic surface will be about 1–10% (w/w), and preferably about 3–5% (w/w).

In order to prevent premature cross-linking, the coating compositions of the present invention do not contain any monomers having more than one unsaturated bond. Such ingredients include the common cross-linking monomers ethyleneglycol dimethacrylate; diethylene glycol dimethacrylate; ethyleneglycol diacrylate; allyl methacrylates; allyl acrylates; 1,3-propanediol dimethacrylate; 1,6-hexanediol dimethacrylate; 1,4-butanediol dimethacrylate; polyethyleneoxide diacrylates; and the like.

The coating compositions optionally include one or more ingredients selected from the group consisting of UV absorbers and blue-light blocking colorants. The UV absorber and/or blue-light blocking colorant may be added either prior to stage 1 polymerization or at the time the stage 1 polymer is dissolved to form a coating solution. If added prior to stage 1 polymerization, the stage 1 polymerization initiator should be chosen so that the UV absorber and/or blue-light blocking colorant do not significantly interfere with the stage 1 polymerization.

Ultraviolet absorbing chromophores can be any compound which absorbs light having a wavelength shorter than about 400 nm, but does not absorb any substantial amount of visible light. It is preferred to use an ultraviolet absorbing compound that is copolymerizable with the monomers of Formula I or the can be covalently bound to the coating/IOL substrate during the second stage cross-linking. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. The most preferred ultraviolet absorbing compound is 2-(3'-methallyl-2'-hydroxy-5'-methyl phenyl) benzotriazole.

If a UV-absorber is added prior to stage 1 polymerization, it is unlikely that a UV polymerization initiator may be used as the first stage polymerization initiator. In such cases, the first stage polymerization initiator will likely have to be either a thermal initiator or a blue-light initiator in order to avoid interference with the UV-absorber.

If a blue-light absorbing compound, e.g. a yellow dye, is included in the coating compositions of the present invention prior to stage 1 polymerization, then the first stage polymerization initiator will likely not be a blue-light photoinitiator. In the event the coating composition contains both a UV-absorber and a blue-light absorbing compound prior to stage 1 polymerization, the first stage polymerization initiator will likely be a thermal initiatior. Preferably, the blue-light absorber is copolymerizable with the monomers of Formula 1 or can be covalently bound to the coating/IOL substrate during the second stage cross-linking. Suitable polymerizable blue-light blocking chromophores include those disclosed in U.S. Pat. No. 5,470,932.

The coating composition of this invention is prepared by forming a mixture comprising, in the desired proportions, the monomers of Formula 1, the first stage polymerization initiator, and optionally one or more of the ingredients selected from the group consisting of second stage cross-linking agents, UV absorbing compounds, and blue-light absorbing compounds. The coating composition is then polymerized by activating (e.g., using heat, UV- or blue-light) the first stage polymerization initiator, being careful not to activate the second stage cross-linking agent, if present.

In the case where the first stage polymerization initiator is a low temperature thermal initiator and the second stage cross-linking agent is dicumyl peroxide, the thermal initiator may be activated by exposure to temperatures of up to approximately 50° C. or so without activating the dicumyl peroxide. In the case where the second stage cross-linking agent is a dibenzoyl peroxide or a substituted dibenzoyl peroxide, the curing temperature for stage 1 will generally be about 40° C. or less. The curing parameters, e.g., length of exposure and temperature or intensity of light source, are preferably chosen to accomplish complete polymerization.

After the first stage polymerization is complete, the resulting polymer is dissolved in a solvent to form a coating solution. Suitable solvents include ketones, such as acetone, methylethylketone and 2-pentanone. The preferred solvent for use with coating compositions consisting essentially of 2-phenylethyl acrylate and 2-phenylethyl methacrylate is 2-pentanone. For the particular coating composition consisting essentially of 2-phenylethyl acrylate and 2-phenylethyl methacrylate, acetone did not work and methylethyl ketone worked only marginally well as a solvent. The solvent should be chosen such that it has an evaporation rate that is neither too fast (resulting in a hazy or frosty coating) nor too slow (meaning the solvent seems to never dry). Additionally, the application time for the coating should be controlled to minimize any swelling of the substrate material so that the there is little or no disturbance of the coating's or substrate's surface. The concentration of the dissolved polymer is not essential, and can be, for example, 5–8% (w/w) of the coating solution. At this time, the second stage cross-linking agent, and any UV absorber or blue-light absorbing compound may be added, if not already contained in the mixture that was polymerized in stage 1.

After the coating solution has been formed, it is applied to the IOL material ("substrate material") to be coated. The substrate material may comprise any ophthalmically acceptable material, such as silicone, hydrogels or hydrophobic acrylic materials. If the substrate is a hydrogel material having a linear swell factor of about 5% or greater, plasticizers should be used to minimize swelling effects during hydration. The plasticizer does not change the water content of the hydrogel material, but changes the swell factor. When hydrated, water exchanges with the plasticizer.

The coatings of the present invention may be used in conjunction with substrate materials intended for use as a "hard" IOL (that is inserted in an unfolded state) or a "foldable" or "soft" IOL (that is inserted in a folded or compressed state). For example, the IOL material to be coated could be those IOL materials disclosed in U.S. Pat. Nos. 5,693,095 or 5,331,073. A preferred IOL material comprises 2-phenylethyl acrylate and 2-hydroxyethyl methacrylate. All that is necessary is that the coating material be different than the IOL material to be coated. Thus, the IOL material to be coated can comprise two or more monomers of formula I, as long as at least one of the two or more monomers of formula I contained in the coating material is different from those comprising the IOL material. The coating may be applied to the portion of the IOL material constituting the optic's entire posterior surface or to only a peripheral band of the posterior surface. Additionally, the optic's anterior surface or a peripheral band of the anterior surface may be coated.

In order to prepare the IOL material to be coated so that it is capable of receiving the coating, it may be necessary or desirable to expose the surface to be coated to a reactive plasma gas prior to applying the coating composition of the present invention. Suitable reactive plasma gases include oxidizing gases, such as oxygen gas. A suitable plasma chamber is the $P^2CIM$ B-Series plasma chamber made by Advanced Plasma Systems, Inc. Using such a chamber, suitable plasma parameters include: power=400 W, plasma gas=oxygen; pressure of the plasma gas=225 mtorr; exposure time=4–6 minutes.

The coating solution may be applied to the IOL material to be coated by dip coating or spin coating, for example. The thickness of the coating should be at least about 0.3 $\mu$m, preferably at least about 1–2 $\mu$m, but may be much thicker if desired. A one-dip coating using a coating solution comprising about 5–8% (w/w) of poly(2-phenylethyl acrylate/2-phenylethyl methacrylate) and about 5% of dibenzoyl peroxide will give approximately a 0.3–0.6 $\mu$m coating.

Once the coating solution has been contacted with the IOL material to be coated, the coating is allowed to air dry and is then secured to the IOL material by activating the second stage cross-linking agent. Activation of the second stage cross-linking agent "secures" the coating to the IOL material by covalently bonding the coating material to the IOL material. Additionally, activation of the second stage cross-linking agent results in cross-linking of the coating material itself. The second stage cross-linking agent can be activated by heating or, particularly for thin (e.g., 0.5 $\mu$m or less) coatings, exposure to electron beam radiation. For example, if the second stage cross-linking agent is dibenzoyl peroxide, the second stage cross-linking agent can be activated by heating at 95–100° C. for approximately four hours in either a vacuum oven (<5 mm Hg) or in an inert (e.g., Argon) atmosphere at atmospheric conditions. The temperature and length of exposure to heat are determined by the identity and amount of the second stage cross-linking agent and the desired degree of cross-linking to be achieved. In general, however, the temperature will be about 90° C. or more where the second stage cross-linking agent is a dibenzoyl peroxide or a substituted dibenzoyl peroxide. In the case where the second stage cross-linking agent is dicumyl peroxide, the activation temperature will be about 125° C. or greater. The duration of heating to achieve the second-stage cross-linking is preferably about four times the half-life of the second stage cross-linking agent at the chosen activation temperature. In the case of dicumyl peroxide and an activation temperature of approximately 135° C., the duration of heating is approximately 4 hours. Electron beam sources are commercially available, and include the Min-EB product available from American International Technologies, Inc.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A coated intraocular lens comprising a substrate material and a coating material for making the intraocular lens more biocompatible and reducing the risk of posterior capsule opacification, wherein the coating material is different than the substrate material and the coating material consists essentially of at least two aryl acrylic hydrophobic monomers of the formula

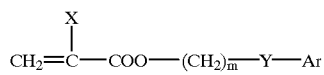

$$CH_2=\overset{X}{\underset{|}{C}}-COO-(CH_2)_{\overline{m}}-Y-Ar \qquad (I)$$

wherein:

X is H or $CH_3$;

m is 0–1;

Y is nothing, O, S, or NR wherein R is H, $CH_3$, $C_nH_{2n+1}$ (n=1–10) iso $OC_3H_7$, $C_6H_5$, or $CH_2C_6H_5$;

Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$.

2. The coated intraocular lens of claim 1 wherein the aryl acrylic hydrophobic monomers of formula I are chosen from the group consisting of 2-phenoxyethyl acrylate; 2-phenylethylthio acrylate; 2-phenylethylamino acrylate; phenyl acrylate; benzyl acrylate; 2-phenylethyl acrylate; 3-phenylpropyl acrylate; 3-phenoxypropyl acrylate; 4-phenylbutyl acrylate; 4-phenoxybutyl acrylate; 4-methylphenyl acrylate; 4-methylbenzyl acrylate; 2-2-methylphenylethyl acrylate; 2-3-methylphenylethyl acrylate; 2-4-methyphenylethyl acrylate; and their corresponding methacrylate compounds.

3. The coated intraocular lens of claim 2 wherein the aryl acrylic hydrophobic monomers of formula I are chosen from the group consisting of 2-phenylethyl acrylate; 2-phenoxyethyl acrylate; 3-phenylpropyl acrylate; 3-phenoxypropyl acrylate; 4-phenylbutyl acrylate; 4-phenoxybutyl acrylate; and their corresponding methacrylate compounds.

4. The coated intraocular lens of claim 1 wherein the aryl acrylic hydrophobic monomers of formula I consist essentially of at least one monomer wherein X=H and at least one monomer wherein X=$CH_3$.

5. The coated intraocular lens of claim 4 wherein the aryl acrylic hydrophobic monomers of formula I are 2-phenylethyl acrylate and 2-phenylethyl methacrylate.

6. The coated intraocular lens of claim 1 wherein the coating material further comprises one or more ingredients selected from the group consisting of UV absorbing compounds and blue-light absorbing compounds.

7. The coated intraocular lens of claim 1 wherein the substrate material is selected from the group consisting of silicone materials, hydrogel materials, and hydrophobic acrylic materials.

* * * * *